(12) United States Patent
Shih et al.

(10) Patent No.: US 6,998,137 B2
(45) Date of Patent: *Feb. 14, 2006

(54) PROTEINS DEPOSITED ONTO SPARINGLY SOLUBLE BIOCOMPATIBLE PARTICLES FOR CONTROLLED PROTEIN RELEASE INTO A BIOLOGICAL ENVIRONMENT FROM A POLYMER MATRIX

(75) Inventors: Chung Shih, Sandy, UT (US); Gaylen Zentner, Salt Lake City, UT (US); Ai-Zhi Piao, Salt Lake City, UT (US)

(73) Assignee: MacroMed, Inc., Sandy, UT (US)

( * ) Notice: Subject to any disclaimer, the term of this patent is extended or adjusted under 35 U.S.C. 154(b) by 59 days.

This patent is subject to a terminal disclaimer.

(21) Appl. No.: 09/827,100

(22) Filed: Apr. 5, 2001

(65) Prior Publication Data

US 2002/0015737 A1 Feb. 7, 2002

Related U.S. Application Data (60) Provisional application No. 60/195,700, filed on Apr. 7, 2000.

(51) Int. Cl.
| | |
|---|---|
| *A61F 2/00* | (2006.01) |
| *A61F 9/14* | (2006.01) |
| *A61F 9/50* | (2006.01) |
| *A61F 47/30* | (2006.01) |
| *A61K 31/74* | (2006.01) |
| *A61K 38/00* | (2006.01) |

(52) U.S. Cl. ............... 424/426; 424/78.08; 424/423; 424/486; 424/489; 424/501; 514/2

(58) Field of Classification Search ............... 424/502, 424/484, 108, 426, 423, 78.08; 514/2
See application file for complete search history.

(56) References Cited

U.S. PATENT DOCUMENTS

| | | | | |
|---|---|---|---|---|
| 4,765,980 | A | * 8/1988 | DePrince et al. | ............ 424/108 |
| 5,688,530 | A | 11/1997 | Bodmer et al. | |
| 6,711,968 | B1 | 1/1998 | Tracey et al. | |
| 5,891,478 | A | * 4/1999 | Johnson et al. | ............ 424/502 |
| 5,912,015 | A | 6/1999 | Bernstein et al. | |
| 6,130,200 | A | * 10/2000 | Brodbeck et al. | ............ 514/2 |
| 6,287,588 | B1 | * 9/2001 | Shih et al. | ............ 424/426 |

OTHER PUBLICATIONS

Cunningham, Brian C. "Dimerization of Human Growth Hormone by Zinc", Science, 253 (pp. 545–547 (1991).*

* cited by examiner

*Primary Examiner*—Shelley A. Dodson
(74) *Attorney, Agent, or Firm*—Thorpe North & Western, LLP (57) ABSTRACT

The present invention relates to compositions and methods for the modulated release of one or more proteins or peptides. The composition is comprised of a biocompatible polymeric matrix, a protein and/or peptide, and a sparingly water-soluble or essentially insoluble particle. The protein is deposited by adsorption or some other mechanism onto the sparingly water-soluble biocompatible particle wherein the protein-particle combination is dispersed within the polymeric matrix. The deposition of the protein onto the particle acts to modulate the release of the protein or peptide from dosage forms including long-acting dosage systems.

31 Claims, 3 Drawing Sheets

PROTEINS DEPOSITED ONTO SPARINGLY SOLUBLE BIOCOMPATIBLE PARTICLES FOR CONTROLLED PROTEIN RELEASE INTO A BIOLOGICAL ENVIRONMENT FROM A POLYMER MATRIX

This application claims the benefit of U.S. Provisional Application No. 60/195,700 filed Apr. 7, 2000.

FIELD OF THE INVENTION

The present invention is related to compositions and methods for the controlled release of proteins from a drug delivery system. Particularly, by depositing proteins onto sparingly water-soluble or essentially insoluble biocompatible particles including salts and oxides, protein release rates from the dosage forms are reduced.

BACKGROUND OF THE INVENTION

There have been many approaches to meet the problems of regulating the delivery of proteins or peptides to biological systems or environments in the proper place, at the proper time, and at the proper dose to achieve a desired effect. These systems generally depend on the utilization of physical or chemical stimuli in the surrounding environment. Further, these environmental stimuli are usually of an external nature to the drug delivery system. Mechanisms that respond to such stimuli or signals include protein binding, hydrogel expanding or swelling, polymer erosion, membrane reorganization, solubility change, energy conversion, supply of activation energy for permeation, physical property changes of the materials that comprise the system, or phase transition phenomena, and the like. Examples are presented in J. Heller, Chemically self-regulated drug delivery systems, J. Control. Rel., 8, 111–125 (1988).

Recently, there has been an increasing interest in developing new protein delivery systems which are both safe and deliver the proteins or peptides in a more controlled manner. Additionally, it has become increasingly desirable to prolong protein delivery over several weeks or even more. Commonly employed pharmaceutical delivery devices include the use of implants, microcapsules, microspheres, and/or nanospheres in the form of nondegradable carriers, biodegradable carriers, or absorbable carriers. Additionally, other microparticle methods of controlled drug release have included the use of micelles, liposomes, etc.

Nondegradeable carriers include silicone rubber, polyethylene, polymethyl methacrylate(PMMA), polystyrene(PST), ethylene-vinyl acetate copolymer(EVA), polyethylene-maleic anhydride copolymers, polyamides, and others. Though, these carriers may be effective and sometimes useful, the implanted or injected compounds remain in the body as a foreign material after release of the protein and may require a surgical procedure for their removal. Additionally, nondegradeable carriers may also cause certain side effects in the body.

Conversely, when using biodegradable and/or absorbable carriers, the carrier is gradually degraded or absorbed in the body simultaneously with or subsequent to the protein release. In fact, biodegradable polymers can be designed to degrade in vivo in a controlled manner over a predetermined time period. Suitable biodegradable polymers for use in such sustained release formulations are well described elsewhere and include polyesters such as poly(D,L-lactide), poly(D,L-lactide-co-glycolide), poly($\epsilon$-caprolactone), poly (hydroxybutylic acid), and poly amino acids, poly(ortho ester)s, polyanhydrides, and poly(alkyl cyanoacrylate)s. These polymers gradually become degraded by enzymatic or non-enzymatic hydrolysis when placed in an aqueous physiological environment. The main mechanism of in vivo degradation for many polymers is hydrolytic degradation in which enzymes may also play a role. Important factors influencing hydrolytic degradation include water permeability, chemical structure, molecular weight, morphology, glass transition temperature, additives, and other environmental factors such as pH, ionic strength, and site of implantation, to name a few.

Whether microparticles, implants, environment responsive gels, or the like are in the form of nondegradable carriers, biodegradable carriers, or absorbable carriers, a unifying principle among all of these drug delivery mediums is a more prolonged and controlled protein delivery process.

Various microencapsulation techniques incorporating a protein or peptide into a microparticle carrier are taught in the prior art. However, microparticles having a biodegradable polymer matrix are especially valuable for reasons suggested above. Methods of making biodegradable microparticles include: (a) phase separation by emulsification and subsequent organic solvent evaporation (including complex emulsion methods such as O/W emulsions, W/O emulsions and W/O/W emulsions), (b) coacervation-phase separation, (c) melt dispersion, (d) interfacial deposition, (e) in situ polymerization, (f) spray drying and spray congealing, (g) air suspension coating, and (h) pan coating, to name a few.

Turning now to biocompatible polymers (including block copolymers, copolymers and the like) capable of existing in a gel state, such polymers are also useful for more prolonged and controlled protein or peptide delivery. In fact, polymers that are sensitive to their environment are especially useful. Environmental conditions that may effect these type of polymers include changes in temperature, pH, ionic strength, solvent, pressure, stress, light intensity, electric field, magnetic field, and/or specific chemical triggers such as glucose. Polymeric gels containing a desired protein or peptide may be administered in a liquid or gel state by a variety of pathways including via parenteral, ocular, topical, transdermal, vaginal, urethral, buccal, transmucosal, pulmonary, transurethral, rectal, intrarespiratory, nasal, oral, aural, sublingual, conjunctival, or by other known methods of administration. Once protein or peptide laden biocompatible and/or biodegradable polymers are administered, the polymer will release the protein or peptide into the body as it biodegrades, is absorbed, or is otherwise reduced to non-toxic products.

Though the aforementioned methods, i.e., microparticles, implants, and environment responsive gel delivery, have been somewhat effective in controlling protein or peptide delivery in the body, there have also been some limitations with these individual technologies. For example, a known problem with many drug delivery systems involve the effect commonly referred to as burst. Burst occurs as the drug delivery system releases more of a bioactive agent, such as a protein, than is desirable at a given time. The result of burst is that the desired uniform delivery of the protein to the body is undermined. In other words, in some cases, biodegradable polymers under in vivo conditions can have an initial level of medicament release (or at some other time) which is too high or too low.

Other limitations include the fact that many biologically active macromolecules, such as proteins and peptides, have low stability. This is particularly true when placed under the harsh fabrication conditions as are present when preparing protein or peptide delivery compositions, e.g., exposure to organic solvents, air-liquid interface, vigorous agitation, sonication, etc. Additionally, many proteins and peptides are highly water soluble.

In the prior art, attempts have been made to stabilize and/or reduce the solubility of proteins and peptides by complexing the proteins or peptides with multivalent cations such as zinc, calcium, magnesium, copper, ferric iron, and nickel, to name a few. For example, zinc complexed insulin is sparingly water-soluble and may be formulated into long-acting depots. Additionally, as disclosed in U.S. Pat. Nos. 5,912,015 and 5,891,478, human growth hormone (hGH) has been complexed with zinc ion to produce a precipitate. This precipitate has been incorporated into microspheres for a one-month sustained delivery in a biological environment. However, neither of these patents disclose the deposit of proteins or peptides onto biocompatible sparingly soluble particles in order to stabilize and/or prolong the release of proteins from a drug delivery biopolymer. Thus, it would be desirable to provide such a composition so that the solubility of the protein and/or the dissolution rate of protein from a drug delivery biopolymer device are reduced.

SUMMARY OF THE INVENTION

The present invention is related to compositions and methods for the modulated release of one or more proteins or peptides in a biological environment. Specifically, a drug delivery system for controlled protein release into a biological environment is disclosed comprising a) a sparingly soluble biocompatible particle; b) an effective amount of a protein or peptide deposited onto the particle forming a substantially insoluble protein-particle combination; and c) a biocompatible polymeric matrix having dispersed therein the protein-particle combination. Though the invention merely calls for the depositing of the protein or peptide onto the particle, one mechanism for deposition is preferably adsorption. Others include absorption and coprecipitation.

By adsorbing the protein or peptide onto the surface of the particle, the protein-particle combination may be incorporated into a long-acting dosage system having a more uniform protein release curve over time than is found in much of the prior art. The present invention also relates to a method for modulating the release of proteins and/or peptides from a biocompatible polymeric matrix.

BRIEF DESCRIPTION OF THE DRAWINGS

In the accompanying drawings which illustrate embodiments of the invention.

DETAILED DESCRIPTION OF THE INVENTION

Before the present invention is disclosed and described, it is to be understood that this invention is not limited to the particular process steps and materials disclosed herein as such process steps and materials may vary to some degree. It is also to be understood that the terminology used herein is used for the purpose of describing particular embodiments only and is not intended to be limiting as the scope of the present invention will be limited only by the appended claims and equivalents thereof.

It must be noted that, as used in this specification and the appended claims, singular forms of "a," "an," and "the" include plural referents unless the content clearly dictates otherwise.

"Biocompatible" shall mean any substance that is not toxic to the body or biological environment. A polymer or polymeric matrix is biocompatible if the polymer, and any degradation products of the polymer, are non-toxic to the recipient or biological environment and also present no significant deleterious effects on the biological environment. A particle is biocompatible if the substance is not toxic to the body or biological environment as the intact particle or as disassociated ions (to extent and at amounts that a sparingly soluble particle may disassociate in a given biological environment).

"Biodegradable" means that the polymer matrix can break down, degrade, or erode within a biological environment to non-toxic components after or while a protein or peptide has been or is being released to form smaller chemical species by enzymatic, chemical, physical, or other process.

"Protein" is intended to include one any of a group of complex organic compounds which contain carbon, hydrogen, oxygen, nitrogen, and sometimes sulfur. Specifically included are any combination of insulin, hormones, vaccines, enzymes, antibiotics, antibodies, neuroactive agents, growth factors, cytokines, antigens, glycoproteins, and other known proteins.

"Biological environment" shall mean any environment, whether in vitro or in vivo, where biological activity may be controlled by protein or peptide release.

The phrase "effective amount" when referring to the protein shall mean a therapeutically, prophylactically, or diagnostically effective amount which can be determined by a person of ordinary skill in the art. If the biological environment is a warm-blooded animal such as a human, factors to consider include body weight, body surface area, age, physical condition, type of agent or protein used, type of polymer used, type of particle used, loading dose and subsequent release levels and rates desired.

"Biocompatible polymeric matrix" or "polymeric matrix" is intended to include any environment responsive polymers or gels (e.g., thermosensitive, pH sensitive, electrical sensitive, etc.), particles, films, pellets, cylinders, discs, implants, microcapsules, microspheres, nanospheres, microparticles, wafers, micelles, liposomes, and other known polymeric configurations used for drug delivery. With respect to forms of microspheres or microencapsulation, generally, the diameter is less than about one millimeter and may have a spherical, non-spherical, or irregular shape.

"Polymeric gel" or "polymer gel" shall mean any polymer, copolymer, block copolymer, and the like that exhibits gelation properties for a period of time when administered within a biological environment, but may be a liquid under conditions not present in that environment.

"Thermosensitive polymeric gel" shall mean any polymeric gel that, depending on temperature, may exist in liquid state or a gel state, including gels having reverse thermal gelation properties.

"Surface" when referring to particles is intended to include any surface point on the particle including surface points within pores.

"Particle" shall mean any substantially insoluble or sparingly soluble particle functional with the present invention. Preferably, the particle is an organic or inorganic salt or oxide particle, though other particles may be functional.

"Sparingly soluble" or "essentially insoluble" when referring to the particles includes highly insoluble salts and oxides as well as particles that are merely substantially insoluble, so long as the particle is insoluble enough to be functional with the present invention. In other words, particles that exhibit some solubility are included as long as they are functional with the present invention. "Protein-particle combination" shall mean the combination or composite between any protein or peptide that is deposited on a sparingly soluble particle such as a salt or oxide particle. One possible mechanism for deposition is adsorption. Other possible mechanisms include absorption and coprecipitation.

"Oxide" and "oxides" is intended to specifically include hydroxides as well as oxides that may be used as the particle to which the protein or peptide is deposited.

"Salt" is intended to include both organic and inorganic salts that may be used as the particle to which the protein or peptide is deposited.

"Warm-blooded animals," in addition to a generally understood meaning, is intended specifically to also include humans.

With this in mind, the present invention is drawn toward compositions and methods for delivering proteins from a drug delivery system such that the control of the level of proteins released is enhanced and the period during which controlled release can be maintained is lengthened. The compositions and methods of the present invention provide a needed improvement over the prior art in that the present compositions reduce the dissolution rate of the protein from the drug delivery system and/or the solubility of the desired protein is also greatly reduced.

Specifically, a drug delivery system for controlled protein release into a biological environment is disclosed comprising a) a sparingly soluble biocompatible particle, including salts and oxides; b) an effective amount of a protein or peptide at least partially deposited onto the particle forming a substantially insoluble protein-particle combination; and c) a biocompatible polymeric matrix having dispersed therein the protein-particle combination.

A method for controlled delivery of a protein to a warm-blooded animal is also disclosed comprising the steps of a) depositing a protein or peptide onto a sparingly soluble biocompatible particle to form a protein-particle combination; b) loading the protein-particle combination in a biocompatible polymeric matrix; and c) administering the loaded biocompatible polymeric matrix to a warm-blooded animal.

Additionally, a method of preparing a protein delivery system is disclosed comprising a) depositing a protein or peptide onto a sparingly soluble biocompatible particle to form a protein-particle combination; and b) loading the protein-particle combination into a biocompatible polymeric matrix.

In any of the compositions and methods of the present invention, the protein-particle combination is preferably prepared at a biocompatible particle to protein or peptide weight ratio from about 1:10 to 100,000:1. Typically, a more practical range of from 1:10 to 1000:1 by weight can be implemented. Additionally, the protein-particle combination should be present in relation to polymeric matrix at from about 0.01 to 30% by weight.

The drug delivery systems and methods described above require the use of a biocompatible sparingly soluble or essentially insoluble particle for the protein to be deposited onto, preferably by adsorption. Exemplary particles include zinc salts and oxides, magnesium salts and oxides, and calcium salts and oxides, provided the salt is biocompatible and is sparingly soluble or essentially insoluble, though other biocompatible sparingly soluble particles may be used. Specifically, preferred particles include zinc carbonate, zinc oxide, zinc tartrate, zinc hydroxide, zinc phosphate, zinc citrate, magnesium oxide, magnesium hydroxide, magnesium carbonate, calcium oxide, calcium phosphate, calcium sulfate, and/or calcium carbonate.

The proteins or peptides that may be deposited onto the particles of the present invention include, but are not limited to, oxytocin, vasopressin, adrenocorticotropic hormone, epidermal growth factor, platelet-derived growth factor (PDGF), prolactin, luteinizing hormone releasing hormone (LHRH), LHRH agonists, LHRH agonists, growth hormones (including human, porcine, and bovine), growth hormone releasing factor, insulin, erythropoietin (including all proteins with erythropoietic activity), somatostatin, glucagon, interleukin (which includes IL-2, IL-11, IL-12, etc.), interferon-$\alpha$, interferon-$\beta$, interferon-$\gamma$, gastrin, tetragastrin, pentagastrin, urogastrone, secretin, calcitonin, enkephalins, endorphins, angiotensins, thyrotropin releasing hormone (TRH), tumor necrosis factor (TNF), parathyroid hormone (PTH), nerve growth factor (NGF), granulocyte-colony stimulating factor (G-CSF), granulocyte macrophage-colony stimulating factor (GM-CSF), macrophage-colony stimulating factor (M-CSF), heparinase, vascular endothelial growth factor (VEG-F), bone morphogenic protein (BMP), hANP, glucagon-like peptide (GLP-1), renin, bradykinin, bacitracins, polymyxins, colistins, tyrocidine, gramicidins, cyclosporins (which includes synthetic analogues and pharmacologically active fragments thereof), enzymes, cytokines, antibodies, vaccines, antibiotics, antibodies, and glycoproteins.

The biocompatible polymeric matrix may come in several configurations within the context of the present invention. For example, the use of environment responsive polymers or gels (e.g., thermosensitive, pH sensitive, electrical sensitive), particles, films, pellets, cylinders, discs, implants, microcapsules, microspheres, nanospheres, microparticles, micelles, and liposomes are exemplary polymeric matrixes that may be used, though other known polymeric configurations may be used. Additionally, the biocompatible polymeric matrix may be in the form of nondegradable polymers, biodegradable polymers, absorbable polymers, and/or bioerodible polymers as are generally known in the art.

If a biodegradable polymer is used for the polymeric matrix, then poly(lactide)s, poly(glycolide)s, poly(lactide-co-glycolide)s, poly(lactic acid)s, poly(glycolic acid)s, poly(lactic acid-co-glycolic acid)s, polyanhydrides, poly(ortho ester)s, polyetheresters, polycaprolactones, polyesteramides, poly($\epsilon$-caprolactone)s, poly(hydroxybutyric acid)s, poly(amino acid)s, poly(alkyl cyanoacrylate)s, and blends and copolymers thereof may be used.

If a block copolymer is used, then block copolymers including A-B-A block copolymers, B-A-B block copolymers, and/or A-B block copolymers are preferred wherein the A block comprises a hydrophobic polymer and the B block comprises a hydrophilic polymer. Particularly, when using one of the aforementioned block copolymers, the most preferred polymeric matrixes are defined where the A block is a biodegradable polymer selected from the group consisting of poly(lactide)s, poly(glycolide)s, poly(lactide-co-glycolide)s, poly(lactic acid)s, poly(glycolic acid)s, poly(lactic acid-co-glycolic acid)s, polyanhydrides, poly(ortho ester)s, polyetheresters, polycaprolactones, polyesteramides, poly($\epsilon$-caprolactone)s, poly(hydroxybutyric acid)s, poly(aminoacids)s, poly(alkyl cyanoacrylate)s, and blends and copolymers thereof, and the B block is polyethylene glycol or monofunctionally derivatized polyethylene glycol such as methoxy polyethylene glycol. Many of these combinations form acceptable thermal reversible gels.

If a nondegradable polymer is to be used, then polyacrylates, polyacrylate esters, silicone rubbers, poloxamers, tetronics, polyethylenes, polymethyl methacrylates, polymethyl methacrylate esters, polystyrenes, ethylene-vinyl acetate copolymers, polyethylene-maleic anhydride copolymers, polyamides, polymers of ethylene-vinyl acetates, acyl substituted cellulose acetates, nondegradable polyurethanes, polyvinyl chlorides, polyvinyl fluorides, poly(vinyl imidazole)s, chlorosulphonate polyolefins, polyethylene oxides, and blends and copolymers thereof are acceptable.

Further, the polymer or polymeric matrix can include blocked, unblocked, or a blend of blocked and unblocked polymers. A blocked polymer is generally defined as having blocked carboxyl end groups. An unblocked polymer is as classically defined in the art, specifically having free carboxyl end groups.

Acceptable molecular weights for polymers may be determined by a person of ordinary skill in the art. Factors that may be considered when determining molecular weights include desired polymer degradation rate, mechanical strength, and rate of dissolution of polymer in solvent. Typically, an acceptable range of molecular weights is of about 2,500 Daltons to about 100,000 Daltons, depending upon which polymer is selected for use, among other factors.

Typically, the compositions and methods of the present invention comprise formulations where a plurality of protein or peptide molecules are present. In such a circumstance, a first portion of the plurality of protein or peptide molecules can be deposited on the particle as part of the protein-particle combination dispersed within the polymeric matrix, and a second portion of the plurality of protein or peptide molecules can be dispersed within the polymeric matrix. Alternatively, multiple types of proteins or peptides can be present as part of a single formulation. For example, a second protein or peptide can be present. In such a circumstance, the second protein or peptide can be deposited on the particle dispersed within the polymeric matrix or be dispersed within the polymeric matrix itself. Typically, the second protein or peptide be present as a plurality of second protein or peptide molecules. Thus, a first portion of the plurality of second protein or peptide molecules can be deposited on the particle as part of a protein-particle combination dispersed within the polymeric matrix, and a second portion of the plurality of second protein or peptide molecules are dispersed within the polymeric matrix.

The composition of this invention can be administered to any biological environment, whether in vitro or in vivo, where controlled protein delivery is desired. For example, the composition could be administered to a human, or other animal, by injection and/or implantation subcutaneously, intramuscularly, intraperitoneally, intradermally, intravenously, intraarterially, or intrathecally, by administration to mucosal membranes, or by in situ delivery to provide the desired dosage of a biologically active agent based on the known parameters for treatment of the various medical conditions with the protein or peptide.

Though the compositions are prepared by depositing proteins and/or peptides onto sparing soluble particles, adsorption of the proteins and/or peptides onto a surface of the particle is a preferred method of accomplishing this. Other deposition methods include absorption and coprecipitation techniques, among others. By depositing the proteins onto sparing water-soluble particles, the protein-particle combination can be incorporated into the drug delivery systems of the present invention.

In U.S. Pat. No. 5,912,015, zinc and magnesium cations were used to modulate the degradation of the polymer matrix and thereby delay the release of biologically active agents, including proteins. However, it was repeatedly stated that the metal cation component must be incorporated separately from the biologically active agent. In the present invention, protein drugs are attached to sparingly soluble particles such as salts or oxides. Therefore, the protein and the sparingly soluble particle are not separate, but physically adjoined. Thus, rather than merely modulating the degradation of the polymer matrix as has been described in the prior art, the particles are functional with respect to the protein or peptide itself as discussed previously.

There are several other reasons why the present invention is an improvement over the prior art. First, as discussed, the water solubility of the proteins or peptides is suppressed so that the proteins or peptides may be incorporated into long-acting formulations. Prior to the present invention, proteins and peptides may have been poor candidates for long-acting dosage drug delivery systems due to this limitation. Second, because proteins tend to aggregate and undergo de-amidation or other forms of undesired change in concentrated states, they are difficult to maintain in their useful form for long periods of time. Due to both of these improvements, a single administration may result in long-term release. Third, such a composition lowers or eliminates the initial bursts that generally occur in such a composition. Thus, high initial peaks and other fluctuations of protein release are reduced. As a practical matter, the proteins or peptides deposited onto these water insoluble particles can also enable the proteins to be stored and processed as dry powders, which is a desirable property for pharmaceutical manufacturers. Thus, the protein-containing particle may easily be incorporated into a drug delivery system. Additionally, the rate of drug release from the drug delivery system can also be controlled by selecting appropriate particles, amount of drug deposited, drug loading parameters, polymeric matrixes, particle sizes, etc.

EXAMPLES

The following examples illustrate the compositions and methods of the present invention. The following examples should not be considered as limitations, but should merely teach how to make the best known drug delivery systems based upon current experimental data.

Example 1
Deposition of hGH onto Zinc Carbonate

Human growth hormone (hGH) (Humatrope®; 5 mg/bottle) was reconstituted with 3 mL of sterile water for injection. About 100 mg of zinc carbonate particles were added and the suspension was allowed to stand in a refrigerator at 4° C. for about 16 hours. After allowing the particles to settle, HPLC analysis of the supernatant was conducted and no detectable levels of hGH were found. The solid material was collected by centrifugation, washed with deionized water, and dried by lyophilization. HPLC analysis showed that the mass balance recovery of hGH, after removal of zinc using EDTA (50 mM), was quantitative.

Example 2
Deposition of hGH onto Zinc Tartrate

A similar procedure as described in Example 1 was followed except that about 100 mg of zinc tartrate was added to the hGH solution instead of zinc carbonate. HPLC analysis of the supernatant was conducted and less than 10% of the added hGH was found. The solid material was collected by centrifugation, washed with deionized water, and dried by lyophilization. HPLC analysis showed that the mass balance recovery of the hGH, after removal of zinc using EDTA (50 mM), was quantitative.

Example 3
Deposition of Insulin onto Zinc Carbonate

About 25 mg of zinc insulin was dissolved in about 25 mL of HEPES buffer (10 mM, pH 6). About 100 mg of zinc carbonate was added and the solution was allow to stand in a refrigerator at 4° C. for over 16 hours. HPLC analysis of the supernatant showed that the concentration of insulin was negligible. The solid material was collected and washed with deionized water and the water was removed by lyophilization. HPLC analysis of the solid material showed that the recovery of insulin was quantitative.

Example 4
Deposition of hGH onto Zinc Carbonate

Several 50 µL aliquots of hGH solution (1.67 mg/mL) were individually placed in 1 mL centrifuge vials. To these solutions, up to 60 µL aliquots of zinc carbonate aqueous suspension (31.54 mg/mL) were added so that the zinc carbonate was present compared to hGH at from 0 to a 22.7:1 ratio by weight. The volume of each vial was adjusted to 110 µL using deionized water. Each mixture was then hand-shaken for 5 minutes and followed by centrifugation. hGH concentration in the supernatant of each was measured by HPLC and the data is shown in FIG. 1.

Figure 1:
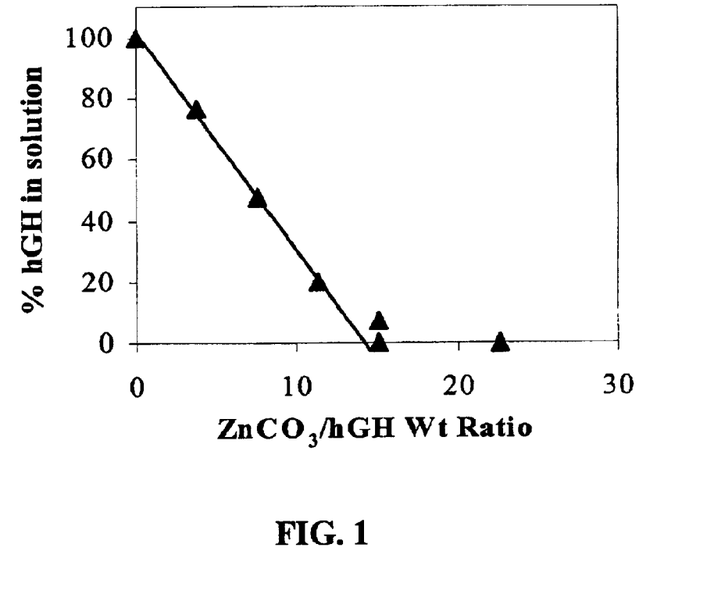
FIG. 1 is a graphical representation depicting the deposition of hGH onto zinc carbonate as a function of the ratio of zinc carbonate to hGH by weight.

Specifially, FIG. 1 depicts the deposition of hGH onto zinc carbonate as a function of the ratio of zinc carbonate to hGH by weight. Essentially complete deposition of hGH onto Zn-carbonate occurred at $ZnCO_3$:hGH weight ratios greater than about 15:1.

Example 5
Deposition of hGH onto Zinc Tartrate

Figure 2:
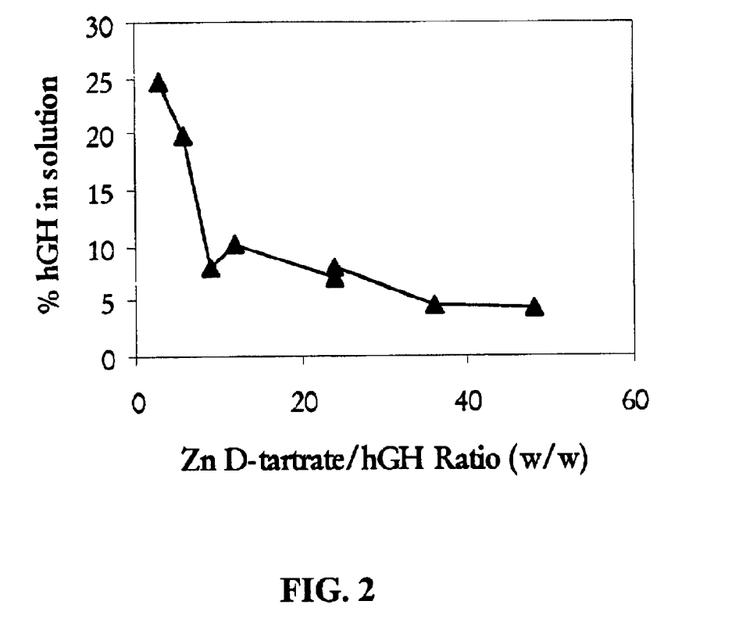
FIG. 2 is a graphical representation depicting the deposition of hGH onto zinc D-tartrate as a function of the ratio of zinc D-tartrate to hGH by weight.

A similar procedure as described in Example 4 was followed except that zinc tartrate was used in place of zinc carbonate. hGH remaining in solution was analyzed by HPLC. hGH concentration in the supernatant was measured by HPLC and the data is shown in FIG. 2.

As shown, the deposition of hGH onto zinc D-tartrate changes as a function of the ratio of zinc D-tartrate to hGH by weight. Greater than 90% of the hGH was deposited onto the zinc tartrate at Zn-tartrate:hGH weight ratios greater than about 10:1.

Example 6
In Vitro Dissolution of hGH and hGH Deposited on Zinc Carbonate hGH/zinc carbonate particles (304 µg of hGH at a 1:20 hGH:$ZnCO_3$ ratio by weight) were placed in a vial and suspended in 100 µL of a thermosensitive tri-block copolymer gel known as ReGel® (20% w/w copolymer in water). ReGel® is biodegradable low molecular weight triblock poly(lactide-co-glycolide) polyethylene glycol copolymer having reverse thermal gelation properties, such as is disclosed in any of U.S. Pat. Nos. 6,201,072, 6,117,949, or 6,004,573. After the gel was set at 37° C., 1 mL of HEPES buffer (10 mM, pH 7.4, containing 0.02% TWEEN-80) was added as the dissolution medium. As a control, this composition was compared to hGH in ReGel® without $ZnCO_3$. Each vial was placed in a 37° C. environment and the entire 1 mL dissolution medium was replaced periodically. hGH in each dissolution medium was measured by HPLC and the data is shown in FIG. 3.

Figure 3:
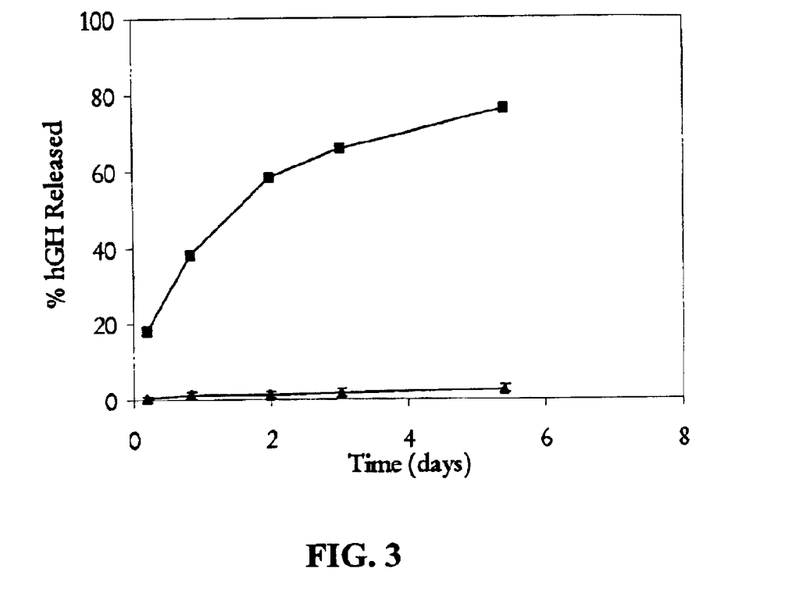
FIG. 3 is a graphical representation depicting the suppression of hGH release from a gel when deposited on zinc carbonate particles.

The legend associated with FIG. 3 is as follows:
- ■=In vitro dissolution (37° C.) of hGH from ReGel® (20% w/w polymer in water) without ZnCO3 into 10 mM Hepes buffer (pH 7.4) containing 0.02% TWEEN-80
- ▲=hGH deposited on zinc carbonate and suspended in ReGel (20% w/w polymer in water) into 10 mM HEPES buffer (pH 7.4) containing 0.02% TWEEN-80

As shown by the data in FIG. 3, hGH release from the gel was significantly suppressed when hGH was deposited on zinc carbonate particles.

Example 7
In Vitro Dissolution of Insulin Deposited on Zinc Carbonate

To 10.22 mL of water was added 32.7 mg of zinc insulin. Complete dissolution was accomplished by addition of 3 drops of acetic acid and allowing the solution to stand in a refrigerator at 4° C. for 16 hours. The solution was then filtered though a 0.2 micron filter. To two 3 mL aliquots of the solution were added 99.5 mg and 30.5 mg of zinc carbonate, respectively. Each mixture was allowed to stand in a refrigerator at 4° C. for about 16 hours. After the suspensions were centrifuged, the insulin levels in each supernatant were found to be negligible by HPLC analysis. The precipitates were washed by deionized water and the water was removed by lyophilization. Solids equivalent to 1 mg of zinc-insulin were placed in 1 mL vials and suspended in 100 µL of a thermosensitive block copolymer gel known as ReGel® (20% w/w copolymer in water). The ReGel® was set in a 37° C. oven and 1 mL of isotonic (NaCl) HEPES buffer solution (10 mM containing 50 mM EDTA, pH 7.4, and 0.02% TWEEN-80) was added as the dissolution medium. Periodically, the entire medium in each solution was replaced by fresh solution. Insulin in each of the dissolution mediums were analyzed by HPLC and the data is presented in FIG. 4.

Figure 4:
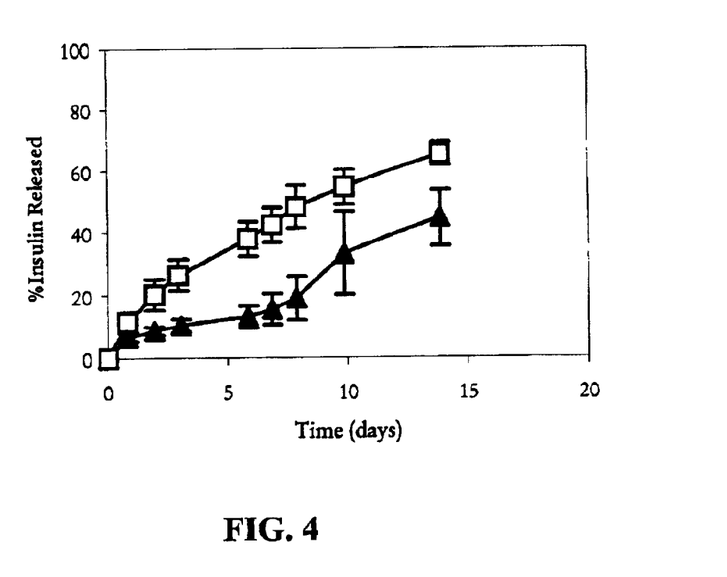
FIG. 4 is a graphical representation depicting the modulation of insulin release as it relates to the weight ratio between the insulin and zinc carbonate particles.

The legend associated with FIG. 4 is as follows:
- □=Dissolution of insulin from insulin/$ZnCO_3$ at 1:3 ratio
- ▲=Dissolution of insulin from insulin/$ZnCO_3$ at 1:10 ratio As shown by the data of FIG. 4, the insulin release was modulated by changing the weight ratio between the insulin and the zinc carbonate.

Example 8
In Vivo Pharmacokinetic Studies of hGH Sustained Release Formulations in Rats Studies were conducted in rats to verify the effect of hGH deposited on sparingly water soluble zinc carbonate salt.

Sprague-Dawley rats were given one of five different formulations having various solution bases. Each formulation contained an equivalent of 55 μg of hGH per 0.3 mL of solution. After subcutaneous administration, blood samples (1 mL) were collected at pre-determined intervals for up to 7 days. Plasma was separated and stored at −40° C. before analysis. hGH concentration in each plasma sample was determined by radioimmunoassay (RIA) using kits obtained from DSL Inc. The control used was a product sold under the trademark Humatrope® by Eli Lilly and Company. The data is shown in FIG. 5.

Figure 5:
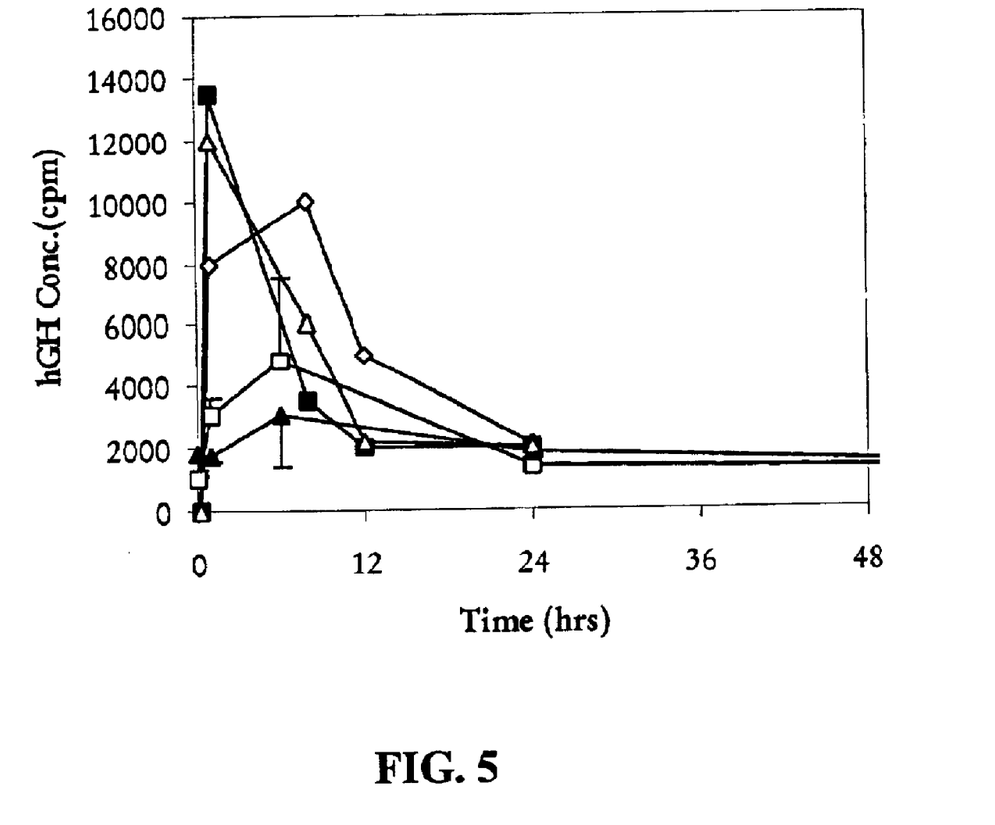
FIG. 5 is a graphical representation depicting the release of hGH in rats delivered from various compositions, including compositions of the present invention.

The legend associated with FIG. 5 is as follows:
∪=Plasma hGH concentration profiles of rats given hGH in diluent
Δ=hGH in 20% ReGel®
◇=zinc-hGH complex suspended in 20% ReGel®
☐=hGH deposited on zinc carbonate particles (hGH:ZnCO$_3$ at a ratio of 1:20 by weight) and suspended in 10 mM HEPES buffer (ph 7.0)
▲=hGH deposited on zinc carbonate particles at a 1:20 ratio by weight and suspended in 20% ReGel®

The data of FIG. 5 indicates that the release of hGH from ReGel® (20%) alone was nearly identical to the control. Suspending zinc-hGH complex in 20% ReGel® delayed the peak plasma level time ($t_{max}$) but did not extend the duration substantially. However, depositing hGH onto zinc carbonate at a 1:20 hGH to zinc carbonate ratio, by weight, (without the presence of ReGel®) not only delayed the time ($t_{max}$), but the peak plasma level ($C_{max}$) was also significantly reduced. Moreover, incorporating hGH-zinc carbonate particles in ReGel® (20% w/w polymer in water) further reduced the peak plasma level ($C_{max}$). this data shows the present invention can modulate release of a protein from a polymeric carrier, and illustrates reduced burst effects and extended duration.

While the invention has been described with reference to certain preferred embodiments, those skilled in the art will appreciate that various modifications, changes, omissions, and substitutions can be made without departing from the spirit of the invention. It is intended, therefore, that the invention be limited only by the scope of the following claims and equivalents thereof.

We claim:

1. A drug delivery system for controlled protein release into a biological environment comprising:
   a) a sparingly soluble biocompatible particle;
   b) an effective amount of a protein or peptide deposited onto the particle forming a substantially insoluble protein-particle combination; and
   c) a biocompatible polymeric matrix having dispersed therein the protein-particle combination.

2. The drug delivery system of claim 1 wherein the protein-particle combination has a biocompatible particle to protein or peptide ratio from about 1:10 to 100,000:1 by weight.

3. The drug delivery system of claim 1 wherein the protein-particle combination has a biocompatible particle to protein or peptide ratio from about 1:10 to 1000:1 by weight.

4. The drug delivery system of claim 1 wherein the protein-particle combination is present in relation to polymeric matrix at from about 0.01 to 30% by weight.

5. The drug delivery system of claim 1 wherein said biocompatible particle is a sparingly soluble salt or oxide selected from the group consisting of zinc salts, zinc oxides, magnesium salts, magnesium oxides, calcium salts, and calcium oxides.

6. The drug delivery system of claim 1 wherein said biocompatible particle is selected from the group consisting of zinc carbonate, zinc oxide, zinc tartrate, zinc hydroxide, zinc phosphate, zinc citrate, magnesium oxide, magnesium hydroxide, magnesium carbonate, calcium oxide, calcium phosphate, calcium sulfate, calcium carbonate, and combinations thereof.

7. The drug delivery system of claim 1 wherein said protein or peptide is selected from the group consisting of oxytocin, vasopressin, adrenocorticotropic hormone, epidermal growth factor, platelet-derived growth factor (PDGF), prolactin, luteinizing hormone releasing hormone (LHRH), LHRH agonists, LHRH agonists, growth hormone, growth hormone releasing factor, insulin, erythropoietin, somatostatin, glucagon, interleukin (including IL-2, IL-11, IL-12, etc.), interferon-α, interferon-β, interferon-γ, gastrin, tetragastrin, pentagastrin, urogastrone, secretin, calcitonin, enkephalins, endorphins, angiotensins, thyrotropin releasing hormone (TRH), tumor necrosis factor (TNF), parathyroid hormone (PTH), nerve growth factor (NGF), granulocyte-colony stimulating factor (G-CSF), granulocyte macrophage-colony stimulating factor (GM-CSF), macrophage-colony stimulating factor (M-CSF), heparinase, vascular endothelial growth factor (VEG-F), bone morphogenic protein (BMP), hANP, glucagon-like peptide (GLP-1), renin, bradykinin, bacitracins, polymyxins, colistins, tyrocidine, gramicidins, cyclosporins, enzymes, cytokines, antibodies, vaccines, antibiotics, antibodies, glycoproteins, and combinations thereof.

8. The drug delivery system of claim 1 wherein said protein is selected from the group consisting of human growth hormone and insulin.

9. The drug delivery system of claim 1 wherein said biocompatible polymeric matrix is selected from the group consisting of polymeric particles, implants, microcapsules, microspheres, nanospheres, polymeric gels, environment responsive polymers or gels, and combinations thereof.

10. The drug delivery system of claim 1 wherein said biocompatible polymeric matrix is comprised of a polymer or gel material selected from the group consisting of non-degradable polymers, biodegradable polymers, absorbable polymers, bioerodible polymers, block copolymers, and combinations thereof.

11. The drug delivery system of claim 10 wherein said biocompatible polymeric matrix is comprised of a biodegradable polymer selected from the group consisting of poly(lactide)s, poly(glycolide)s, poly(lactide-co-glycolide)s, poly(lactic acid)s, poly(glycolic acid)s, poly(lactic acid-co-glycolic acid)s, polyanhydrides, poly(ortho ester)s, poly (ε-caprolactone), poly(hydroxybutyric acid), polyaminoacids, and blends and copolymers thereof.

12. The drug delivery system of claim 10 wherein said biocompatible polymeric matrix is a block copolymer selected from the group consisting of A-B-A block copolymers, B-A-B block copolymers, A-B block copolymers, and combinations thereof, and wherein said A block is a biodegradable polymer selected from the group consisting of poly(lactide)s, poly(glycolide)s, poly(lactide-co-glycolide)s, poly(lactic acid)s, poly(glycolic acid)s, poly (lactic acid-co-glycolic acid)s, polyanhydrides, poly(ε-caprolactone)s, poly(hydroxybutyric acid)s, poly (aminoacids)s, poly(ortho ester)s, and blends and copolymers thereof, and said B block is polyethylene glycol.

13. The drug delivery system of claim 10 wherein said biocompatible polymeric matrix is comprised of a nondegradable polymer selected from the group consisting of polyacrylates, polyacrylate esters, silicone rubbers, poloxamers, tetronics, polyethylenes, poly(methyl methacrylate)s, polymethyl methacrylate esters, polystyrenes, ethylene-vinyl acetate copolymers, polyethylene-maleic anhydride copolymers, polyamides, polymers of ethylene-vinyl acetates, acyl substituted cellulose acetates, nondegradable polyurethanes, poly(vinyl chloride)s, poly(vinyl fluoride)s, poly(vinyl imidazole)s, chlorosulphonate polyolefins, poly(ethylene oxide)s, and blends and copolymers thereof.

14. The drug delivery system of claim 1 wherein the protein or peptide is deposited onto a surface of the particle.

15. A method of preparing a protein delivery system comprising:
   a) depositing a protein or peptide onto a sparingly soluble biocompatible particle to form a protein-particle combination; and
   b) loading the protein-particle combination in a biocompatible polymeric matrix.

16. The method of claim 15 wherein the protein-particle combination has a biocompatible particle to protein or peptide ratio from about 1:10 to 100,000:1 by weight.

17. The method of claim 15 wherein the protein-particle combination has a biocompatible particle to protein or peptide ratio from about 1:10 to 1000:1 by weight.

18. The method of claim 15 wherein the protein-particle combination is present in relation to polymeric matrix at from about 0.01 to 30% by weight.

19. The method of claim 15 wherein the protein or peptide is deposited onto the particle by a mechanism selected from the group consisting of adsorption, absorption, and coprecipitation.

20. The method of claim 15 wherein the protein or peptide is deposited onto a surface of the particle.

21. The method of claim 15 wherein said biocompatible particle is a sparingly soluble salt or oxide selected from the group consisting of zinc salts, zinc oxides, magnesium salts, magnesium oxides, calcium salts, and calcium oxides.

22. The method of claim 15 wherein said sparingly soluble particle is selected from the group consisting of zinc carbonate, zinc oxide, zinc tartrate, zinc hydroxide, zinc phosphate, zinc citrate, magnesium oxide, magnesium hydroxide, magnesium carbonate, calcium oxide, calcium phosphate, calcium sulfate, calcium carbonate, and combinations thereof.

23. The method of claim 15 wherein said protein or peptide is selected from the group consisting of oxytocin, vasopressin, adrenocorticotropic hormone, epidermal growth factor, platelet-derived growth factor (PDGF), prolactin, luteinizing hormone releasing hormone (LHRH), LHRH agonists, LHRH agonists, growth hormone, growth hormone releasing factor, insulin, erythropoietin, somatostatin, glucagon, interleukin (including IL-2, IL-11, IL-12, ect,), interferon-α, interferon-β, interferon-γ, gastrin, tetragastrin, pentagastrin, urogastrone, secretin, calcitonin, enkephalins, endorphins, angiotensins, thyrotropin releasing hormone (TRH), tumor necrosis factor (TNF), parathyroid hormone (PTH), nerve growth factor (NGF), granulocyte-colony stimulating factor (G-CSF), granulocyte macrophage-colony stimulating factor (GM-CSF), macrophage-colony stimulating factor (M-CSF), heparinase, vascular endothelial growth factor (VEG-F), bone morphogenic protein (BMP), hANP, glucagon-like peptide (GLP-1), renin, bradykinin, bacitracins, polymyxins, colistins, tyrocidine, gramicidins, cyclosporins, enzymes, cytokines, antibodies, vaccines, antibiotics, antibodies, glycoproteins, and combinations thereof.

24. The method of claim 15 wherein said protein is selected from the group consisting of human growth hormone and insulin.

25. The method of claim 15 wherein said biocompatible polymeric matrix is selected from the group consisting of polymeric particles, implants, microcapsules, microspheres, nanospheres, polymeric gels, environment responsive polymers or gels, and combinations thereof.

26. The method of claim 15 wherein said biocompatible polymeric matrix is comprised of a polymer material selected from the group consisting of nondegradable polymers, biodegradable polymers, absorbable polymers, bioerodible polymers, block copolymers, and combinations thereof.

27. The method of claim 26 wherein said biocompatible polymeric matrix is comprised of a biodegradable polymer selected from the group consisting of poly(lactide)s, poly(glycolide)s, poly(lactide-co-glycolide)s, poly(lactic acid)s, poly(glycolic acid)s, poly(lactic acid-co-glycolic acid)s, polyanhydrides, poly(ortho ester)s, poly(ε-caprolactone), poly(hydroxybutyric acid), polyaminoacids, and blends and copolymers thereof.

28. The method of claim 26 wherein said biocompatible polymeric matrix is a block copolymer selected from the group consisting of A-B-A block copolymers, B-A-B block copolymers, A-B block copolymers, and combinations thereof, and wherein said A block is a biodegradable polymer selected from the group consisting of poly(lactide)s, poly(glycolide)s, poly(lactide-co-glycolide)s, poly(lactic acid)s, poly(glycolic acid)s, poly(lactic acid-co-glycolic acid)s, polyanhydrides, poly(ε-caprolactone)s, poly(hydroxybutyric acid)s, poly(aminoacids)s, poly(ortho ester)s, and blends and copolymers thereof, and said B block is polyethylene glycol.

29. The method of claim 26 wherein said biocompatible polymeric matrix is comprised of a nondegradable polymer selected from the group consisting of polyacrylates, polyacrylate esters, silicone rubbers, poloxamers, tetronics, polyethylenes, poly(methyl methacrylate)s, polymethyl methacrylate esters, polystyrenes, ethylene-vinyl acetate copolymers, polyethylene-maleic anhydride copolymers, polyamides, polymers of ethylene-vinyl acetates, acyl substituted cellulose acetates, nondegradable polyurethanes, poly(vinyl chloride)s, poly(vinyl fluoride)s, poly(vinyl imidazole)s, chlorosulphonate polyolefins, poly(ethylene oxide)s, and blends and copolymers thereof.

30. A drug delivery system for controlled protein release into a biological environment comprising:
   a) a sparingly soluble biocompatible particle selected from the group consisting of zinc salts, zinc oxides, magnesium salts, magnesium oxides, calcium salts, calcium oxides, and combinations thereof;
   b) an effective amount of a protein or peptide deposited onto the particle forming a substantially insoluble protein-particle combination, wherein the protein-particle combination has a biocompatible particle to protein or peptide ratio from about 1:10 to 100,000:1 by weight; and
   c) a biocompatible polymeric matrix having dispersed therein the protein-particle combination, wherein the protein-particle combination is present in relation to polymeric matrix at from about 0.01 to 30% by weight.

31. A drug delivery system for controlled protein release into a biological environment comprising:
  a) a sparingly soluble biocompatible particle;
  b) an effective amount of a protein or peptide deposited onto the particle forming a substantially insoluble protein-particle combination; and
  c) a biocompatible polymeric matrix said comprised of a polymer or gel material selected from the group consisting of nondegradable polymers, biodegradable polymers, absorbable polymers, bioerodible polymers, block copolymers, and combinations thereof, said polymeric matrix in a form selected from the group consisting of polymeric particles, implants, microcapsules, microspheres, nanospheres, polymeric gels, environment responsive polymers or gels, and combinations thereof, said polymeric matrix having dispersed therein the protein-particle combination.

* * * * *